United States Patent [19]
Matsuo et al.

[11] Patent Number: 5,360,727
[45] Date of Patent: Nov. 1, 1994

[54] C-TERMINAL α-AMIDATING ENZYME AND PROCESS FOR PRODUCTION THEREOF

[75] Inventors: Hisayuki Matsuo, 6653, Ooaza Kihara, Kiyotake-cho, Miyazaki-gun, Miyazaki 889-16; Kensaku Mizuno; Masayasu Kojima, both of Miyazaki, all of Japan

[73] Assignee: Hisayuki Matsuo, Miyazaki, Japan

[21] Appl. No.: 921,600

[22] Filed: Aug. 3, 1992

Related U.S. Application Data

[63] Continuation of Ser. No. 322,568, Mar. 13, 1989, abandoned.

[30] Foreign Application Priority Data

Mar. 14, 1988 [JP] Japan .................. 63-58187

[51] Int. Cl.$^5$ .............. C12N 9/02; C12N 9/00; C12P 21/00
[52] U.S. Cl. ............... 435/189; 435/183; 435/68.1
[58] Field of Search ............ 435/68.1, 183, 189

[56] References Cited

U.S. PATENT DOCUMENTS 4,708,934 11/1987 Gilligan et al. .............. 435/68.1
4,921,797 5/1990 Matsuo et al. .............. 435/129

FOREIGN PATENT DOCUMENTS 8404756 12/1984 WIPO .............. C12N 15/00
8701729 3/1987 WIPO .............. C12P 21/02

OTHER PUBLICATIONS

Bradbury et al. (1982) *Nature*, 298, 686–688.
Kizer et al. (1984) *Proc. Natl. Acad. Sci. USA.*, 81, 3228–3232.
Stoffers et al. (1989) *Proc. Natl. Acad. Sci. USA*, 86, 735–739.
Eipper et al. (1985) *Endocrinology*, 116(6), 2497–2504.
Eipper et al. (1988) *J. Biol. Chem.*, 263(17), 8371–8379.
Sakata et al. (1986) *Biochem. Biophys. Res. Comm.*, 140(1), 230–236.

(List continued on next page.)

*Primary Examiner*—Irene Marx
*Assistant Examiner*—Jon P. Weber
*Attorney, Agent, or Firm*—Burns, Doane, Swecker & Mathis

[57] ABSTRACT

The invention relates to a C-terminal α-amidating enzyme of porcine origin having the following properties: (1) the action is on a peptide or protein represented by the formula:

X-R-Gly, wherein Gly represents a C-terminal glycine residue, R represents an amino acid residue to be α-amidated, and X represents a remaining portion of the peptide or protein to convert it to a peptide or protein represented by the formula:

X-R-NH$_2$, wherein R-NH$_2$ represents a C-terminal α-amidated amino acid residue and X represents a remaining portion of the peptide or protein; (2) the optimal pH is 6.5 to 8.5; (3) the molecular weight is about 92,000 as determined by SDS-polyacrylamide gel electrophoresis; and (4) it contains the following peptide fragment:

... Glu-Ala-Pro-Leu-Leu-Ile-Leu-Gly ....

Further, the invention relates to a process for the production of the C-terminal α-amidating enzyme comprising the steps of extracting and purifying the enzyme from porcine atrium cordis exhibiting the enzyme activity.

1 Claim, 7 Drawing Sheets

OTHER PUBLICATIONS

Eipper et al. (1987) *Mol. Endorpinol.* 1(11), 777–790 in *Chem. Abst.*, 111(5), Abst. #34395.

"Mechanism of C-Terminal Amide Formation by Pituitary Enzymes", Alan F. Bradbury et al., *Nature*, vol. 298, (1982), pp. 686–688.

"Enzyme-catalysed Peptide Amidation", Alan F. Bradbury et al., *Eur. J. Biochem.*, vol. 169, (1987), pp. 579–584.

"Identification in Pituitary Tissues of a Peptide α-Amidation Activity that acts on Glycine-Extended Peptides and Requires Molecular Oxygen, Copper, and Ascorbic Acid", Betty A. Eipper et al., *Prod. Natl. Acad. Sci.*, vol. 80 (1983), pp. 5144–5148.

"Detection and Partial Characterization of an Amidating Enzyme in Skin Secretion of *Xenopus laevis*", Christa Mollay et al., *FEBS*, vol. 202, No. 2 (1986) pp. 251–254.

"Post-translational Processing in Xenopus Oocytes Includes Carboxyl-Terminal Amidation", Mary M. Bendig, *The Journal of Biological Chemistry*, vol. 261, No. 26 (1986), pp. 11935–11937.

"Peptide C-Terminal α-Amidating Enzyme Purified to Homogeneity from *Xenopus Laevis* Skin", Kensaka Mizuno et al., *Biochem. Biophys. Res. Comm.*, vol. 137, No. 3 (1986), pp. 984–981.

"Cloning and Sequence of cDNA Encoding a Peptide C-Terminal α-Amidating Enzyme from *Xenopus Laevis*", Kensaka Mizuno, et al., *Biochem. Biophys. Res. Comm.*, vol. 148, No. 2 (1987), pp. 546–552.

"Cloning of cDNA Encoding a New Peptide C-Terminal α-Amidating Activity in Rat", Junichiro Sakata et al., *Biochem. Biophys. Res. Comm.*, vol. 140, No. 1 (1986), pp. 230–236.

"Tissue Distribution and Characterization of Peptide C-Terminal α-Amidating Activity in Rat", Junichiro Sakata et al., *Biochem. Biophys. Res. Comm.*, vol. 140, No. 1 (1986), pp. 230–236.

"Structure of the Precursor to an Enzyme Mediating COOH-Terminal Amidation in Peptide Biosynthesis", Betty A. Eipper et al., *Molecular Endocrinology*, vol. 1, (1987), pp. 777–790.

"Membrane-associated Forms of Peptidylglycine α-Amidating Monooxygenase Activity in Rat Pituitary", Victor May et al., *The Journal of Biological Chemistry*, vol. 263, No. 16 (1988), pp. 7550–7554.

"Membrane-associated Peptidylglycine α-Amidating Monooxygenase in the Heart", Betty A. Eipper et al., *The Journal of Biological Chemistry*, vol. 263, No. 17 (1988), pp. 8371–8379.

"A New Facile Trinitrophenylated Substrate for Peptide α-Amidating and its Use to Characterize PAM Activity in Chromaffin Granules", Andreas G. Katopodis et al., *Biochem. Biophys. Comm. Res.*, vol. 151, No. 1 (1988), pp. 499–505.

"Glycine-directed Peptide Amidation: Presence in Rat Brain of Two Enzymes that Convert p-Glu-His-Pro—Gly-OH into p-Glu-His-Pro-NH$_2$ (Thyrotropin-Releasing Hormone)", J. S. Kizer et al., *Proc. Natl. Acad. Sci.*, vol. 81 (1984), pp. 3228–3232.

"Characterization of a Substance P-Gly$^{12}$ Amidating Enzyme in Human Cerebrospinal Fluid", Henning Vaeroy et al., *Biochem. Biophys. Comm. Res.*, vol. 148, No. 1 (1987), pp. 24–30.

"Purification of a Peptidylglycine α-Amidating Enzyme from Transplantable Rat Medullary Thyroid Carcinomas", Nozer M. Mehta, *Archives of Biochemistry and Biophysics*, vol. 261, No. 1 (1988), pp. 44–54.

"Peptidyl-Glycine α-Amidating Mono-Oxygenase Activity Towards a Gonadotropin-Releasing Hormone C-Terminal Peptide Substrate, in Subcellular Fractions of Sheep Brain and Pituitary", Jean S. Gale et al., *Biochem. J.*, vol. 251 (1988), pp. 251–259.

"Evidence of High Peptide α-Amidating Activity in the Pancreas from Neonatal Rats", L'Houcine Ouafik et al., *Proc. Natl. Acad. Sci.*, vol. 84, (1987), pp. 261–264.

C-TERMINAL α-AMIDATING ENZYME AND PROCESS FOR PRODUCTION THEREOF

This application is a continuation, of application Ser. No. 07/322,568, filed Mar. 13, 1989, now abandoned.

BACKGROUND OF THE INVENTION

1. Field of the Invention

The present invention relates to a C-terminal α-amidating enzyme of porcine origin and a process for the production thereof.

2. Related Art

Recently it was found that various peptides and proteins isolated from the nerves and endocine systems have a C-terminal amino acid, the α-carboxyl group of which is amidated ($-CONH_2$), and that this structure is often essential for physiological activities of the peptides and proteins. A general biosynthesis mechanism of such amidated peptides is understood to be that in which RNA is translated to a precursor of an amidated peptide, which is then amidated at the α-position of its C-terminal by a C-terminal α-amidating enzyme. Note, in the above-mentioned reaction, the precursor of the C-terminal α-amidated peptide as a substrate for a C-terminal α-amidating enzyme is a peptide or protein represented by a general formula X-R-Gly, wherein R represents an amino acid residue which is to be α-amidated at the C-terminal thereof, Gly represents a glycine residue, and X represents a remaining part of the peptide or protein.

Because of the importance of clarifying the mechanism of α-amide formation in tissues, and the promising usefulness of the enzyme for the production of C-terminal α-amidated peptides using, for example, recombinant DNA techniques, many attempts to purify the enzyme have been made but the enzyme has not so far been obtained in a pure state. In porcine pituitary, Bradburg, A. F. et al, Nature, 298, 686–688, 1982, first characterized the α-amidating activity of converting a synthetic substrate D-Tyr-Val-Gly to D-Tyr-Val-$NH_2$, and demonstrated that the C-terminal glycine in the substrate serves as a nitrogen-donor for α-amidation. Eipper et al, Proc. Natl. Acad. Sci. US, 80, 5144–5148, 1983, reported that the α-amidating enzyme derived from the pituitary gland requires a copper cation and ascorbate for its activity. Husain, I. et al., FEBS Lett., 152 227–281, 1983; and Kizer, J. S. et al, Proc. Natl. Acad. Sci. US, 81, 3228–3232, 1984, also reported a C-terminal α-amidating enzyme, but did not report a purified enzyme. Recently, Murthy A. S. N. et al, J. Biol. Chem. 261, 1815–1822, 1986, partially purified a C-terminal α-amidating enzyme from the pituitary gland of cattle, and showed that several types of enzymes having different molecular weights and electric charges are present. Nevertheless, no type of enzyme has been homogeneously purified.

Recently, Mizuno et al. succeeded in isolating a C-terminal α-amidating enzyme in a homogeneous and pure form from a skin of *Xenopus laevis*; see Mizuno, K. et al, Biochem. Biophys. Res. Commun. 137, 984–991, 1988, and Japanese Patent Application No. 61-131089, and further succeeded in determining an entire primary amino acid sequence of the C-terminal α-amidating enzyme of a skin of *Xenopus laevis* origin by obtaining and sequencing cDNA; see Mizuno, K. et al, Biochem. Biophys. Res. Commun. 148, 546–552, 1987. Nevertheless, since proteins exhibiting a C-terminal α-amidating activity in mammalian tissues are present in a very small amount, are unstable, and are not homogeneous, it is very difficult to isolate and purify such proteins from the mammalian tissues, and no one has succeeded in this to date. Therefore, currently it is not clear whether there is one or more than one C-terminal α-amidating enzyme in a mammal, and if there is more than one enzyme, whether these enzymes have the same or a different substrate specificity.

SUMMARY OF THE INVENTION

The present inventors studied the distribution of the C-terminal α-amidating enzyme in a rat, and found that the desired enzyme activity is present in the atrium cordis; See Sakata, J. et al., Biochem. Biophy. Res. Common. 140, 230–236, 1986. The present inventors expanded this study to those of porcine origin, and found that the C-terminal α-amidating enzyme activity is present in the atrium cordis of porcine; which is advantageous in that the porcine atria is easier to obtain in larger amounts than the rat atria. Subsequently, the enzyme was extracted and purified from the porcine atria and a confirmed to be a homogeneous new enzyme.

Accordingly, the present invention provides a C-terminal α-amidating enzyme of porcine origin having the following properties:

(1) Action and substrate specificity: acting on a peptide or protein represented by the formula:

X-R-Gly 

wherein Gly represents a C-terminal glycine residue, R represents an amino acid residue to be α-amidated, and X represents a remaining portion of the peptide or protein to correct same to a peptide or a protein represented by the formula:

X-R-$NH_2$ 

wherein R-$NH_2$ represents a C-terminal α-amidated amino acid residue and R represents a residual portion of the peptide or protein;

(2) optimum pH: 6.5 to 8.5;
(3) molecular weight: about 92,000 as determined by SDS-polyacrylamide gel electrophoresis;
(4) containing the following peptide fragment:

... Glu-Ala-Pro-Leu-Leu-Ile-Leu-Gly ... 

Moreover, the present invention provides a process for the production of the C-terminal α-amidating enzyme comprising the step of extracting and purifying the enzyme from porcine atrium cordis exhibiting the enzyme activity.

DESCRIPTION OF THE PREFERRED EMBODIMENTS

The C-terminal α-amidating enzyme of the present invention has the following properties.

(A) Action and Substrate Specificity

The present enzyme acts on a peptide or protein having a glycine residue at its C-terminal as a substance and converts the peptide or protein to a peptide or protein α-amidated at its C-terminal but lacking the C-terminal glycine residue. Namely, the present enzyme acts on a peptide or protein represented by the formula:

wherein Gly represents C-terminal glycine residue, R represents an amino acid residue to be α-amidated and X represents a remaining portion of the peptide or protein to connect it to a peptide or protein represented by the formula:

wherein R-NH$_2$ represents a C-terminal α-amidated amino acid residue and R represents a residual portion of the peptide or protein. The glycine residue is essential and serves as an N atom donor for the amide formation.

(B) Molecular Weight

The enzyme has a molecular weight of about 92,000 as determined by SDS-polyacrylamide gel electrophoresis using molecular weight standards, myosin 200,000, β-galactosidase 116,250; phosphorylase B 92,500, bovine serum albumin 66,200; and ovalbumin 45,000.

(C) Optimum pH

Figure 9:
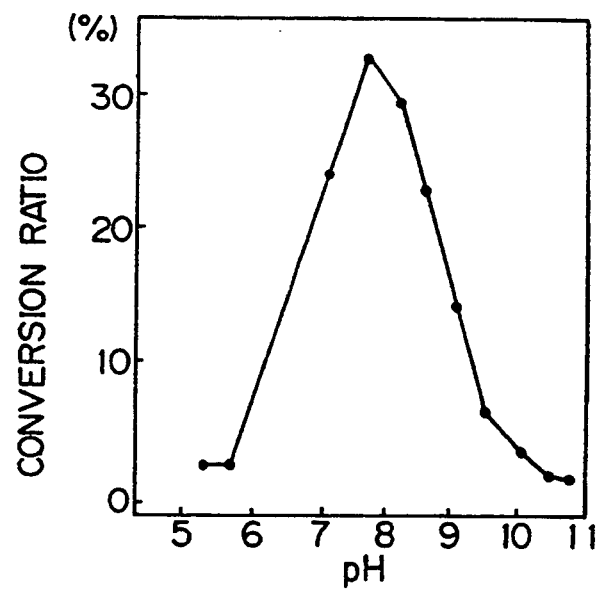
FIG. 9 shows the relationship between the enzyme activity and pH value.

The enzyme has an optimum pH range of 6.5 to 8.5 as shown in FIG. 9.

(D) Response to Enzyme Activity to Various Agents (1) $Cu^{++}$ ion is essential to the enzyme activity. Although the enzyme is inhibited by EDTA, the addition to $CuSO_4$ at a concentration higher than that of the EDTA restores the enzyme activity.

(2) The enzyme activity is inhibited by dithiothreitol, but the enzyme activity inhibited by dithiothreitol is restored by the presence of N-maleimide or $CuSO_4$ at a concentration higher than that of dithiothreitol.

(3) The enzyme activity is lower in the absence of ascorbic acid in an enzyme reaction mixture.

(E) Amino Acid Sequence

A tryptic fragment of the present enzyme has the following amino acid sequence:

... Glu-Ala-Pro-Leu-Leu-Ile-Leu-Gly ...

The present enzyme can be produced as follows, wherein porcine atria are used as tissues for an extraction of the enzyme. The porcine atria are washed with an appropriate buffer, and disrupted with an appropriate physical means to extract the desired enzyme, which is then recovered from the extract and purified by a conventional procedure. For example, the extract is centrifuged to obtain a precipitate, which is then washed with a buffer. The washed precipitate is centrifuged to obtain a precipitate, which is then treated with a surfactant followed by centrifugation to obtain a supernatant containing the desired enzyme. The supernatant is applied to a DEAE Sepharose DE-25 column, which is then eluted using sodium chloride linear gradient. Next, active fractions of the elute are applied to a Q-Sepharose Fast Flow column (Pharmacia), which is then eluted using sodium chloride linear gradient. The obtained active fractions of the elute are applied to Affi-Gel Blue (Bio-Rad), and a flow through fraction is subjected to affinity chromatography using a Try-Phe-Gly-CH-Sepharose column. Finally, the elute is subjected to gel filtration to obtain the purified C-terminal α-amidating enzyme of the present invention.

In examples of the present invention, a C-terminal α-amidating enzyme of the present invention is assayed using synthetic peptide, [$^{125}$I]-Ac-Tyr-Phe-Gly as a substrate, according to the following procedure. [$^{125}$I]-Ac-Tyr-Phe-Gly (1 pmole, 70,000–150,000 cpm) is incubated with an enzyme preparation, in a final volume of 250 μl containing 0.2M Tris-HCl buffer (pH 7.0), 2 μM $CuSO_4$, 0.25 mM ascorbic acid, 25 μg catalase (Boehringer), and 0.1% Lubrol (PX type, Nakarai Chemicals). The reaction mixture is kept at 37° C. for 1 to 3 hours, and then 0.75 ml of 1M Tris-HCl buffer (pH 7.0) and 2 ml of the organic phase of an ethyl acetate/water mixture is added. The two phases are mixed vigorously in a Vortex mixer, and after centrifugation at 3000 rpm for 3 mins, the organic phase thus separated is transferred to another test tube. The radioactivity in the organic and aqueous layers is measured by a gamma scintillation counter. Under the conditions described above, over 98% of the radioactivity of the authentic [$^{125}$I]-Ac-Tyr-Phe-Gly is retained in an aqueous phase and over 98% of the radioactivity of the authentic [$^{125}$I]-Ac-Tyr-Phe-NH$_2$ is transferred to an organic phase.

The yield of conversion is calculated from the ratio of the radioactivity in the ethyl acetate phase to the total radioactivity. In this assay, one unit is defined as the enzyme activity that gives a fifty percent conversion of 1 pmole substrate [$^{125}$I]-Ac-Try-Phe-Gly to [$^{125}$I]-Ac-Tyr-Phe-NH$_2$ for one hour.

By using the enzyme of the present invention, a peptide or protein represented by the formula X-R-Gly can be converted to a corresponding C-terminal amidated peptide or protein represented by the formula X-R-NH$_2$. Note, although herein the present enzyme was extracted and purified from the porcine atrium, since the present invention discloses a portion of the amino acid sequence of the present enzyme, it is possible to design a probe to screen cDNA derived from porcine atrium to obtain a cDNA coding for the C-terminal α-amidating enzyme, which cDNA can be then used to produce a recombinant C-terminal α-amidating enzyme.

EXAMPLES

The present invention will now be further illustrated by, but is by no means limited to, the following examples.

Example 1.

Extraction and Purification of C-terminal α-amidating Enzyme from Porcine Atria 1 kg in wet weight of porcine atria was homogenized in 10 l of 10 mM Tris-HCl (pH 7.0) buffer using a Polytron homogenizer, and the homogenate was centrifuged to obtain a precipitated fraction. The fraction was extracted with 5 l of the above-mentioned buffer, and the mixture was centrifuged at 12,000×g for 30 minutes to obtain a precipitate. The precipitate was then extracted with 5 l of 10 mM Tris-HCl (pH 8.0) containing 0.1% Lubrol, and the extraction mixture was centrifuged at 12,000 g for 30 minutes to obtain a supernatant. This supernatant was applied to a column (4.5 cm×63 cm) filled with DEAE cellulose DE52 which had been equilibrated with the buffer, and the adsorbed materials were eluted with 4 l of linear gradient 0–0.3M sodium chloride in Tris-HCl buffer (pH 8.0). The elution profile is shown in FIG. 1.

Figure 1:
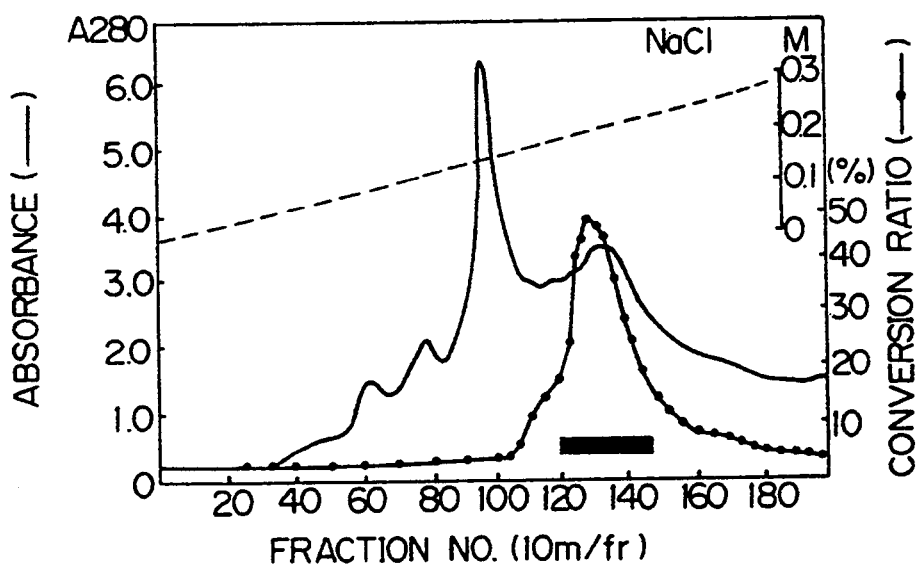
FIG. 1 shows an elution profile of column chromatography using DEAE-cellulose DE-52, wherein a crude extract from a porcine atria homogenate was fractionated.

It was found that the fractions Nos. 120–145 in FIG. 1 exhibited desired activity, and these fractions were combined and dialyzed in 10 mN Tris-HCl (pH 8.0) buffer containing 0.1% Lubrol. To the dialyzate, two protease inhibitors, i.e., leupeptin and phenylmethylsulfonyl fluoride were added to a final concentrations of 50 mM and 0.5 mM, respectively. Next, this mixture was applied to a column (2 cm×35 cm) filled with Q-Sepharose Fast Flow previously equilibrated with 10 mM Tris-HCl (pH 8.0) buffer containing 0.1% Lubrol. After the column was washed with the same buffer, the adsorbed materials were eluted using 2 l of linear gradient 0–0.5M sodium chloride Tris-HCl buffer (pH 8.0). The elution profile is shown in FIG. 2.

Figure 2:
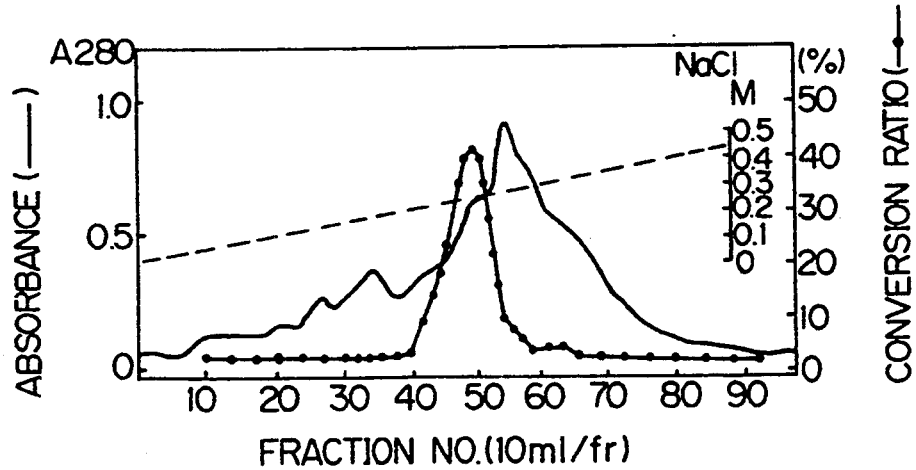
FIG. 2 shows an elution profile of column chromatography using Q-Sepharose, wherein an elute from the fractions No. 125 to 145 shown in FIG. 1 was fractionated after treatment.
Figure 3:
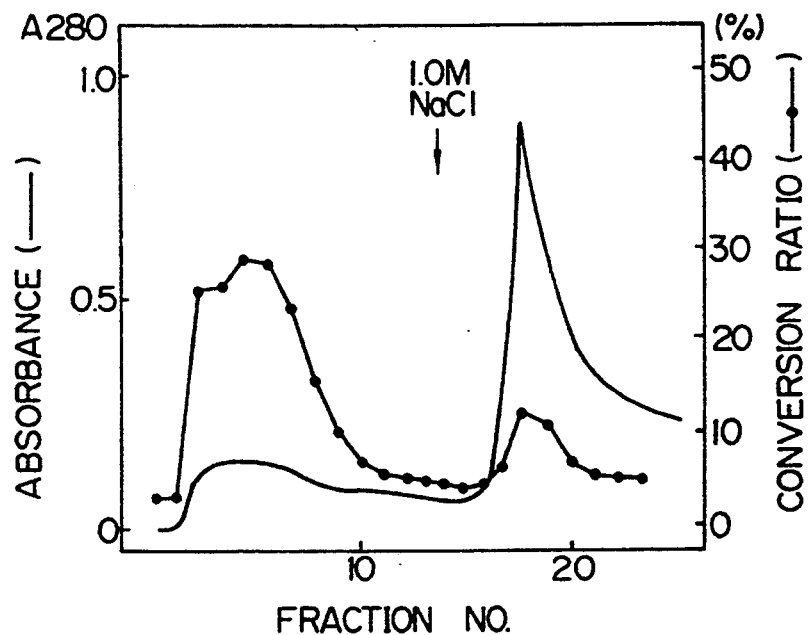
FIG. 3 shows an elution profile of column chromatography using Affi-Gel Blue, wherein an elution from the fractions 43 to 54 shown in FIG. 2 was fractionated.
Figure 4:
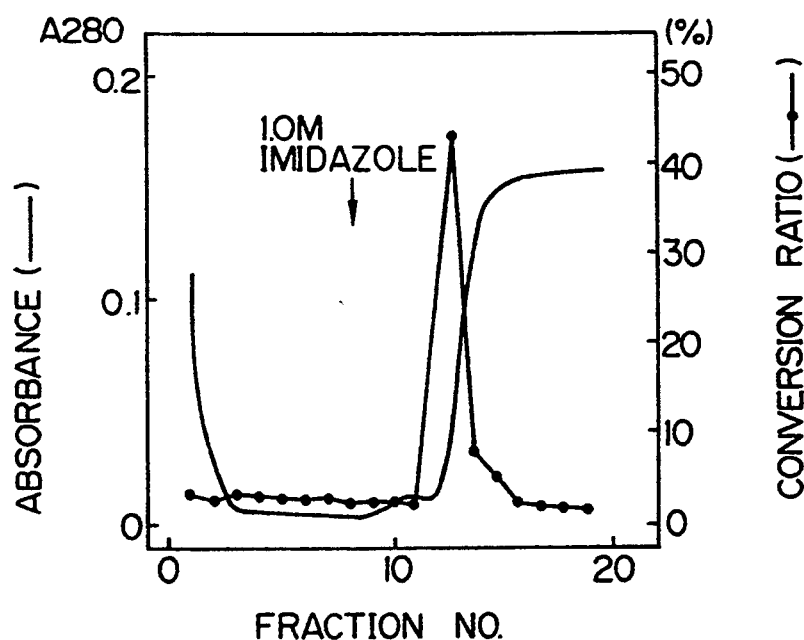
FIG. 4 shows a elution profile of column chromatography using Tyr-Phe-Gly-CH-Sepharose, wherein fractions exhibiting the enzyme activity shown in FIG. 3 were fractionated.

Fractions Nos. 43–54 in FIG. 2, which exhibited the enzyme activity, were combined, and diluted with the same volume of 10 mM Tris-HCl buffer (pH 8.0) containing 0.1% Lubrol. The diluted mixture was applied to a column (1.7 cm×11 cm) filled with Affi-Gel Blue (Bio-Rad) previously equilibrated with 10 mM Tris-HCl (pH 8.0) containing 0.1% Lubrol and 0.1M NaCl to collect a flow through fraction (FIG. 3). The fraction was immediately applied to an affinity column, i.e., a column (0.7 cm×5 cm) filled with Tyr-Phe-Gly-CH-Sepharose previously equilibrated with the same buffer containing 0.2M NaCl, and the active fraction was eluted with 1M imidazole (pH 7.0) containing 0.1% Lubrol. The elution profile is shown in FIG. 4.

Figure 5:
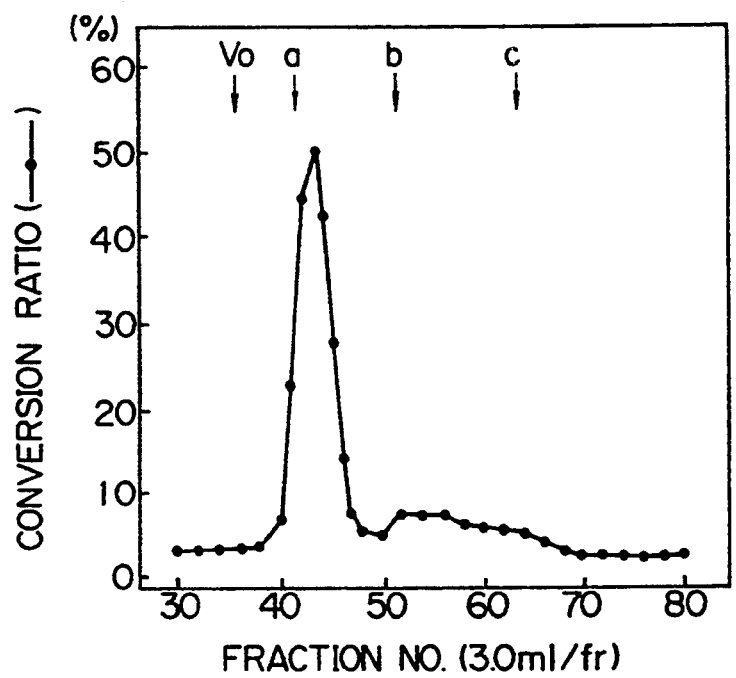
FIG. 5 shows a elution profile for final purification by column chromatography using Sephadex G-100, wherein the fraction exhibiting the desired enzyme activity was purified. In this figure, the arrows a, b, and c represent positions at which standard proteins elute, wherein a corresponds to γ-globulin, b corresponds to bovine serum albumin, and c corresponds to ovalbumin.

Next, the active fraction thus obtained was finally purified using a column (1.8 cm×130 cm) filled with Sephadex G-100 previously equilibrated with 50 mM Tris-HCl (pH 7.0) buffer containing 0.1% Lubrol and 0.2M NaCl by gel filtration, and the fractions Nos. 41–45 were combined to obtain a purified enzyme fraction of the present invention. The results are shown in FIG. 5. In FIG. 5, the arrows a, b, and c represent the elution positions of standard proteins, i.e., γ-globulin (a), bovine serum albumin (b), and ovalbumin (c).

The following Table 1 summarizes the whole process described above for purification of the present invention, wherein the total protein, total activity of C-terminal α-amidating enzyme specific activity, yield, and extent of purification are shown.

TABLE 1

| Step | Total protein (mg) | Total activity (unit) | Specific activity (unit/mg) | Yield | Extent of purification (times) |
|---|---|---|---|---|---|
| 1. Crude extract | 29960 | 788 × 10³ | 26.3 | (100.0) | (1.0) |
| 2. DE-52 | 1594 | 172 × 10³ | 108 | 21.8 | 4.1 |
| 3. Q-Sepharose Fast Flow | 467.6 | 121 × 10³ | 259 | 15.4 | 9.8 |
| 4. Affi-Gel blue | 111.0 | 115 × 10³ | 1040 | 14.6 | 39.5 |
| 5. Substrate affinity | | (4685) | | | |
| 6. G-100 | 0.028 | 7060 | 252000 | 0.96 | 9680 |

Note, in steps 1 and 2, to prevent an effect of thiol compound on the enzyme reaction, the enzyme reaction mixture contained 10 mM N-ethylmaleimide. In all steps other than steps 5 and 6, the total protein was determined by absorbance at 280 nm. In step 5, the total protein and correct enzyme activity could not be determined due to the inhibitory action of imidizole on the α-amidation. In step 6, the protein concentration was determined by SDS-PAGE.

Figure 6:
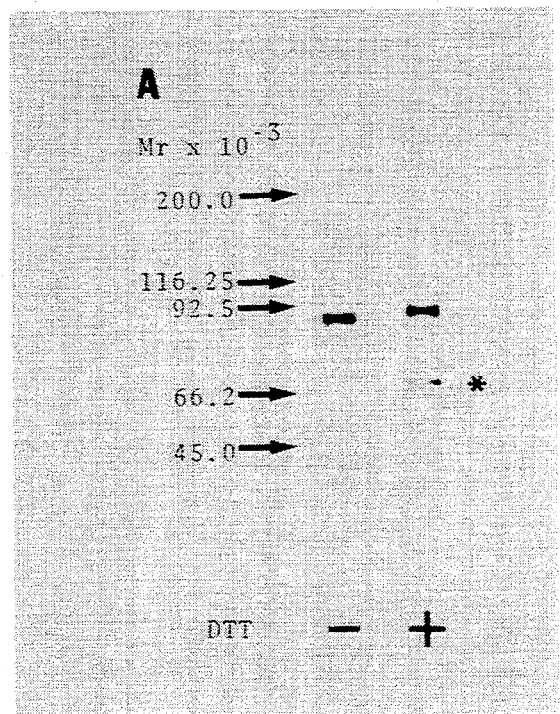
FIG. 6 represents an SDS-polyacrylamide gel electrophoresis pattern on 4–20% concentration gradient polyacrylamide gel using a discontinuous eluent system in the presence or absence of dithiothreitol (DTT)
Figure 7:
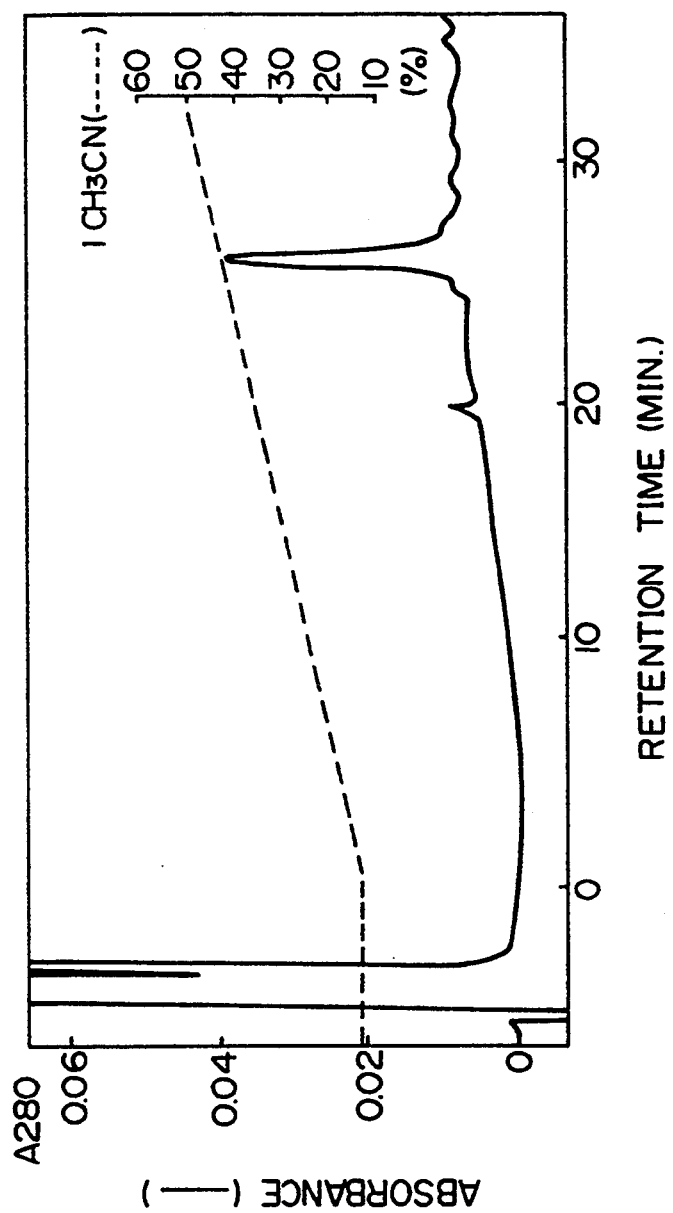
FIG. 7 shows an elution profile of reverse high performance liquid chromatography (HPLC) using TSK Phenyl-5PW to confirm the homogenity of the finally purified enzyme preparation of the present invention.

To confirm the purity of the obtained enzyme preparation, the preparation was analyzed by reverse HPLC using TSK Phenyl-5PW (Toso, Japan). Namely, 2 μg of the purified enzyme was applied to a column (4.6 cm×75 cm) filled with TSK Phenyl-5PW, and eluted with linear gradient of 10% to 60% CH$_3$CH in 0.1% trifluoroacetic acid (TFA) at a flow rate of 1.0 ml/minutes, for 40 minutes. The fractions were analyzed for α-amidation activity by the above-mentioned method, and it was found that a single peak detected by absorbance at 280 nm matches the active fraction. The results are shown in FIG. 7. Moreover, the purified enzyme preparation was subjected to SDS-electrophoresis on a 4 to 20% polyacrylamide gradient gel discontinuous buffer system in the presence and absence of dithiothreitol (DTT), and separated protein were stained by silver staining. The results are shown in FIG. 6. Regardless of the presence or absence of the DTT, the present enzyme exhibited a band corresponding to a molecular weight of about 92,000. In this experiment, molecular weight standards myosin 200,000; β-galactosidase 116,250;phosphorylase B 92,500; bovine serum albumin 66,200; and ovalbumin 45,000 were used.

Example 2.

Analysis of Amino Acid Sequence

15 μg of the purified enzyme was dissolved in 100 μl of 5 mM Tris-HCl (pH 8.0) buffer containing 2 mM $CaCl_2$, and reacted with 300 mg of TPCK-treated trypsin (Worthington) at 37° C. for 12 hours. To the reaction mixture, further 300 ng of TPCK-treated trypsin was added, and a reaction was carried out for 12 hours. The reaction mixture was applied to a Chemcosorb 3 ODS-H column (8×75 mm, Chemco) equilibrated with 0.1% TFA, and elution was carried out using linear gradient of 0 to 60% CH3CH at a flow rate of 2 ml/minute, for 80 minutes. The amino acid sequence of one of the tryptic fragments thus prepared was analyzed using a Protein Sequencer 470A (Applied Biosystems), and as a result, the following sequence:

... Glu-Ala-Pro-Leu-Leu-Ile-Leu-Gly ...

was obtained.

Example 3.

Figure 8A:
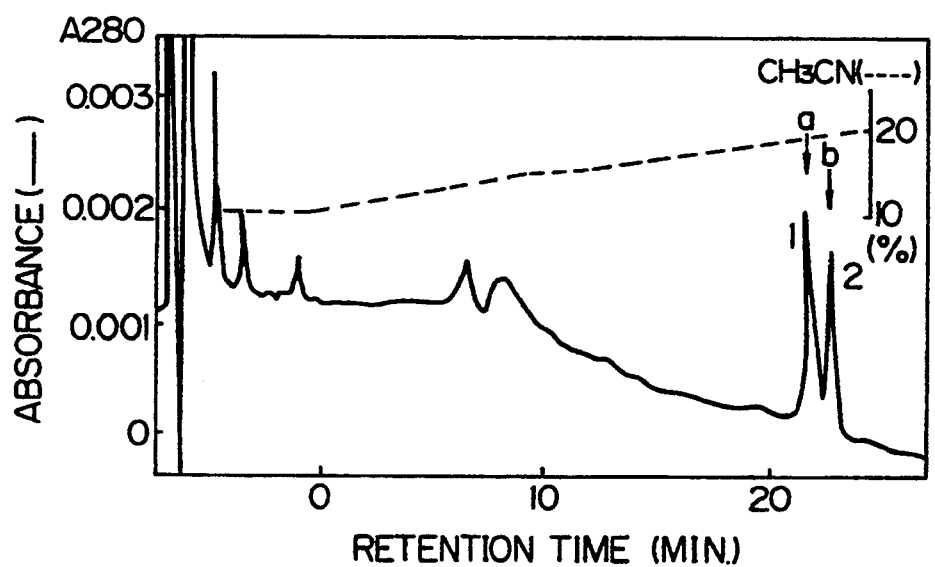
FIG. 8 shows a result of column chromatography using TSK ODS-120A of enzyme reaction products, wherein A represents an elution profile of the product from an enzyme reaction in which the enzyme preparation acted on the substrate peptide Ac-Tyr-Phe-Gly, and B represents an elution profile of the product from an enzyme reaction in which the present enzyme preparation acted on the substrate peptide Tyr-Gly-Gly-Phe-Met-Arg-Arg-Val-Gly. In the figure, the arrows a, b, c, and d represent elution positions of authentic peptides, Ac-Tyr-Phe-NH$_2$, Ac-Tyr-Phe-Gly, Tyr-Gly-Gly-Phe-Met-Arg-Arg-Val-NH$_2$, and Tyr-Gly-Gly-Phe-Met-Arg-Arg-Val-Gly, respectively.
Figure 8B:
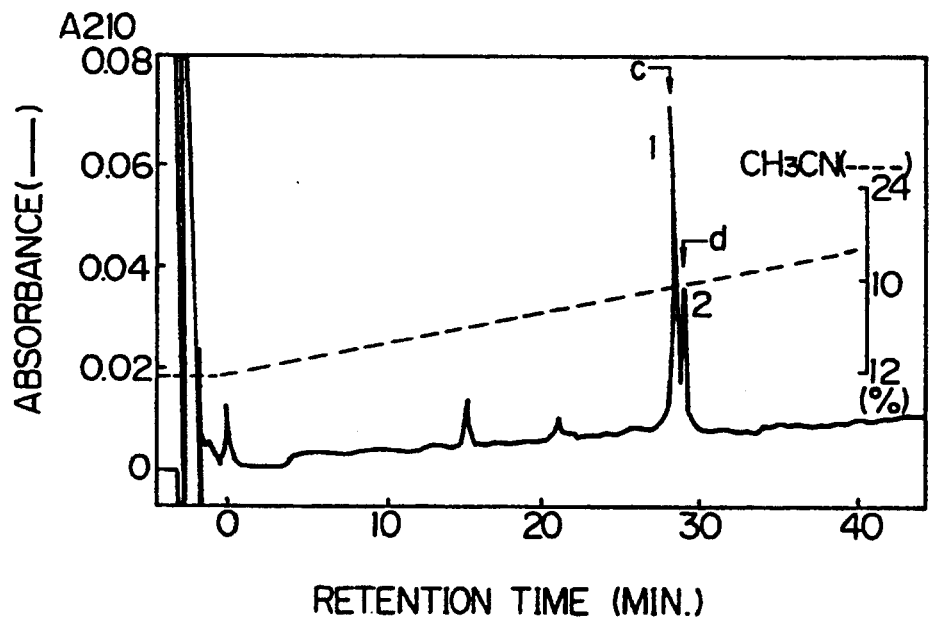

Confirmation of Enzyme Activity 0.1 μg of the C-terminal α-amidating enzyme was reacted with 4 nmole of a substrate (A) Ac-Tyr-Phe-Gly, or (B) Tyr-Gly-Gly-Phe-Met-Arg-Arg-Val-Gly in 0.2M Tris-HCl (pH 7.0), 2 μM $CuSO_4$, 0.25M ascorbic acid, 25 μg catalase and 0.1% Lubrol at 37° C. for 24 hours. After an addition of 250 μl to 1% trifluoroacetic acid (TFA) to the reaction mixture to terminate the reaction, the reaction mixture was applied to a TSK ODS-120A column (Toso, 0.4 cm×25 cm), and elution was carried out using linear gradient of 10 to 60% CH3CN in 0.1% TFA for 120 minutes for (A), and 12 to 60% CH2CN is 0.1% TFA for 192 minutes for (B), both at a flow rate of 1.5 ml/min. Peptides in an elute were followed by a measurement of absorbance at 210 nm, and expected peaks 1 and 2 were found. Namely, on the basis of the amino acid composition, C-terminal amide analysis, and retention time in HPLC, compared with those of authentic peptides, the peaks were identified as follows: A (1)=Ac-Tyr-Phe-NH2; A 2=Ac-Try-Phe-Gly; (B) 1=Tyr-Gly-Gly-Phe-Met-Arg-Arg-Val-NH2; and B 2=Tyr-Gly-Gly-Phe-Met-Arg-Arg-Val-Gly. Note, elution positions of the authentic peptides are shown by the arrows "a", "b", "c", and "d" in FIG. 8, wherein "a" corresponds to Ac-Tyr-Phe-NH2; "b" corresponds to Ac-Tyr-Phe-Gly; "c" corresponds Tyr-Gly-Gly-Phe-Met-Arg-Arg-Val-NH2; and "d" corresponds Tyr-Gly-Gly-Phe-Met-Arg-Arg-Val-Gly.

As seen above, the substrate (A) was converted to a corresponding peptide lacking the glycine residue in (A) and having an amidated C-terminal α-carboxyl group; and the substrate (B) was converted to a corresponding peptide named Adrenorphin, lacking the glycine residue in (B) and having an amidated C-terminal α-carboxyl group.

Example 4.

Effect of pH Value and Ascorbic Acid Concentration on C-terminal α-amidation Activity The α-amidating activity of the present invention under different pH values and different ascorbic acid concentrations was measured by the above-mentioned method. In the experiment shown in FIG. 9, the pH was adjusted by an acetate buffer (pH 4.0 to 5.0), $K_2HPO_4$—$KH_2PO_4$ buffer (pH 5.0 to 7.0), Tris-HCl buffer (pH 7.0 to 9.0), and $Na_2CO_3$—$NaHCO_3$ buffer (pH 9.0 to 11.0).

Figure 10:
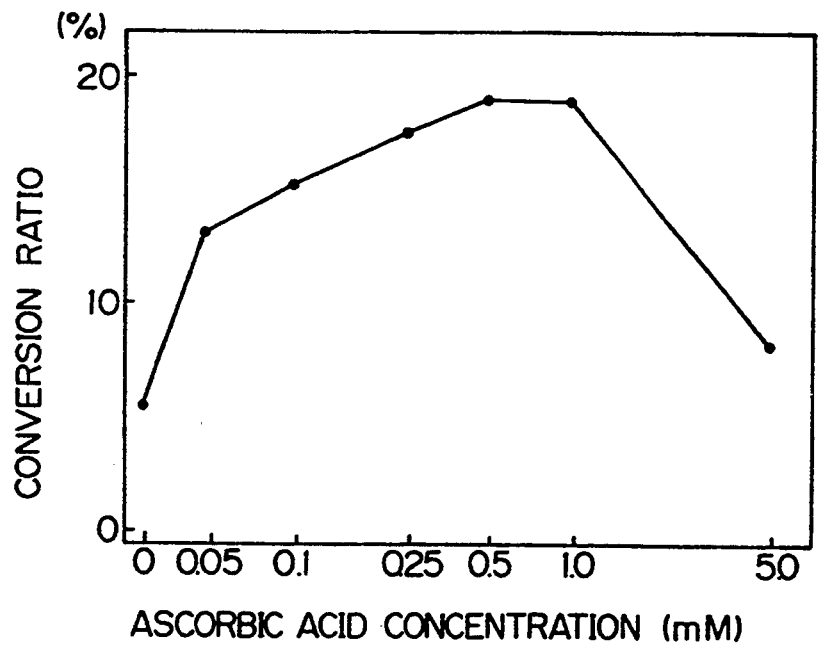
FIG. 10 shows the relationship between the enzyme activity and ascorbic acid concentration.

As seen from FIG. 9, the optimum pH range of the present invention is from 6.5 to 8.5. FIG. 10 shows that the enzyme activity is remarkably lowered in the absence of ascorbic acid.

We claim:

1. A substantially purified C-terminal α-amidating enzyme of porcine atria origin having the following properties:

(1) Action and substrate specificity: acting on a peptide or protein represented by the formula:

X-R-Gly wherein Gly represents a C-terminal glycine residue, R represents an amino acid residue to be α-amidated, and X represents the remaining portion of the peptide or protein to convert it to a peptide or protein represented by the formula

X-R-NH2 wherein R-NH2 represents the C-terminal α-amidated amino acid residue and X represents the remaining portion of the peptide or protein;

(2) optimum pH: 6.5–8.5;
 (3) molecular weight: about 92,000 as determined by SDS-polyacrylamide gel electrophoresis; and
 (4) containing the following peptide fragment:

... Glu-Ala-Pro-Leu-Leu-Ile-Leu-Gly ....

\* \* \* \* \*